United States Patent
Mohr et al.

(12)

(10) Patent No.: US 6,299,737 B1
(45) Date of Patent: Oct. 9, 2001

(54) RECOVERY OF GLYCOLS FROM USED GLYCOL-CONTAINING TECHNICAL FLUIDS

(75) Inventors: Jürgen Mohr, Grünstadt; Wolf-Dieter Balzer, Ludwigshafen, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/420,077

(22) Filed: Apr. 11, 1995

(30) Foreign Application Priority Data

Apr. 18, 1994 (DE) ................................................. 44 13 419
Nov. 21, 1994 (DE) ................................................. 44 41 371

(51) Int. Cl.[7] .............................. B01D 3/34; B01D 3/36; C07C 27/30
(52) U.S. Cl. ................................ 203/69; 203/18; 203/37; 203/57; 203/71; 568/868
(58) Field of Search ................................ 203/51, 57, 69, 203/63, 67, 18, 71, 60, 36–37; 568/871, 913, 868; 252/380

(56) References Cited

U.S. PATENT DOCUMENTS

| | | |
|---|---|---|
| 3,809,724 | 5/1974 | Golden . |
| 3,878,055 * | 4/1975 | Cox et al. ................................ 203/37 |
| 3,968,174 | 7/1976 | Kollar . |
| 3,968,175 | 7/1976 | Kollar . |
| 4,021,311 | 5/1977 | Becker . |
| 4,057,471 | 11/1977 | Chueh . |
| 4,151,048 | 4/1979 | Becker et al. . |
| 4,187,153 | 2/1980 | Peltzman et al. . |
| 4,276,126 | 6/1981 | Saffer . |
| 4,382,008 * | 5/1983 | Boreland et al. ....................... 252/75 |
| 4,810,404 * | 3/1989 | Gausetis et al. ....................... 252/75 |
| 4,935,102 | 6/1990 | Berg . |
| 4,946,595 * | 8/1990 | Miller, Jr. ............................ 210/651 |
| 4,966,658 | 10/1990 | Berg . |
| 4,980,033 * | 12/1990 | Berg ....................................... 203/69 |
| 5,064,552 * | 11/1991 | Oppenlaender et al. .............. 252/75 |
| 5,391,263 | 2/1995 | Hepner et al. . |

FOREIGN PATENT DOCUMENTS

0788398 * 3/1973 (BE) .
40 30 331   3/1992 (DE) .

* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for recovering glycols from used glycol-containing technical fluids, especially from used antifreeze comprises adding to the used glycol-containing technical fluids an organic solvent which forms with the glycol to be separated off an azeotropic mixture which has a lower boiling point than the glycol itself and distilling off this azeotropic mixture.

5 Claims, No Drawings

RECOVERY OF GLYCOLS FROM USED GLYCOL-CONTAINING TECHNICAL FLUIDS

The present invention relates to an improved process for recovering glycols from used glycol-containing technical fluids, especially from used antifreeze.

Large amounts of antifreeze are used. After use, it may contain, in addition to water, up to 50% by weight of glycols, especially ethylene glycol and propylene glycol, and specific additives, but also, according to origin and field of use, specific contaminants. Other glycol-containing technical fluids may contain, in addition to water, up to 90% by weight of glycols. For this reason used antifreeze must not simply be allowed to pass into the environment, but has to be specially disposed of or else recycled.

Further, large amounts of liquids containing glycol, especially ethylene glycol, are obtained in the manufacture of polyesters, especially polyester fibers; these liquids also contain, in addition to water, other impurities stemming from the process.

In the case of recycling, the chief concern is to recover the glycol components, especially ethylene glycol. Recovering the additive components as well as specific contaminants does not make technical sense because of their multitude and variety. But it is specifically these ingredients which, because of their physical and chemical properties, can appreciably hinder or impair the recovery of the glycols from the used antifreeze.

A number of methods have been developed for removing the glycols from the used antifreeze by simple distillation at atmospheric pressure or reduced pressure, as described for example in DE-A-40 30 331.

In principle, distillation is the processing method of choice. However, it is always associated with the imposition on the material being processed of a certain thermal stress, which causes the actual problems.

The abovementioned additives are usually organic and inorganic solids which, on distillation, will gradually accumulate in the bottom product and settle out. This gives rise to clumping, encrustation and caking in the heated parts of the distillation plant. This is the case even when, instead of a simple batch distillation, a thin-film or falling-film evaporator is used.

In consequence, the high thermal stress gives rise to decomposition reactions whose products reappear in the glycol distillate and have an adverse effect on its properties even in trace amount.

For instance, the inorganic nitrites frequently present in antifreeze as corrosion inhibitors can combine with organic nitrogen compounds to form nitrosamines. For this reason the distillation of the used antifreeze should be preceded by a reduction of the nitrites. Since the known methods for reducing nitrites almost all operate in an acid medium, but antifreeze is at best neutral or usually even alkaline, complete reduction requires the addition of an acid. The attendant salt formation additionally worsens the above-described situation of the distillation.

The intrinsically actually very effective way of getting rid of the nitrosamines by boiling in a strongly alkaline medium is not advisable because of the known safety risks of concentrating glycol bottoms.

The other additives and the contaminants from the use of the antifreeze, too, interfere with the used antifreeze processing and glycol recovery. Used antifreeze, for example from the automotive sector, contains, as a consequence of its use, contaminants such as solids through abrasion of metals and sealing materials, and also mineral oil and lubricant constituents. Lack of care in collecting the used antifreeze, however, may also mean that, for example, paint residues, cleaners and-used oils are present as contaminants.

Altogether these components have a color—but especially also an odor-conferring effect on the recovered glycols—and the higher the processing temperature, the greater the effect.

Virtually all recycled glycols have a more or less pronounced, very typical and usually very unpleasant odor.

It is an object of the present invention to provide a recycling process which is free of the above-described problems and which yields pure, colorless and odorless glycol recyclate in as simple a manner as possible.

We have found that this object is achieved by a process for recovering glycols from used glycol-containing technical fluids, especially from used antifreeze, which comprises adding to the used glycol-containing technical fluids an organic solvent which forms with the glycols to be separated off an azeotropic mixture which has a lower boiling point than the glycol itself and distilling off this azeotropic mixture.

Of particular suitability are those azeotropes which, on the one hand, have an atmospheric pressure boiling point which is not too high, i.e. still distinctly below the boiling point of glycols themselves, and, on the other, contain high glycol contents and which have miscibility gaps, in particular at low temperatures.

Organic solvents which form binary azeotropic mixtures with glycols, especially with ethylene glycol, include in particular toluene, o-chlorotoluene, o-bromotoluene, styrene, o-toluidine, n-octanol, 1,2-dibromo-ethane, $1,2$-dibromobutane, amyl acetate and dichloromethane.

In principle, the azeotropic mixtures can also be distilled off at subatmosphere pressure to lower the boiling points, thus working under milder conditions and using less energy.

An extremely suitable organic solvent is pseudocumene (1,2,4-trimethylbenzene), which has a particularly high proportion of ethylene glycol in the azeotrope.

However, the best results are obtained with xylenes; it is customary to use the technical grade mixture of o-, m- and p-xylene. For instance, xylenes and ethylene glycol form azeotropic mixtures having glycol contents from 15 to 20% by weight and boiling at from 130 to 140° C. At room temperature, the mixtures separate into two phases. Glycol can therefore be continuously separated off. The xylenes are recirculated for continuous entrainment, so that comparatively little entraining agent is needed for the gentle processing of large quantities of glycol.

It is also possible to use mixtures of the organic solvents mentioned, for example to form ternary azeotropic mixtures.

The glycols to be recovered from the used antifreeze include ethylene glycol as main component or even as almost the sole component; in addition propylene glycol, diethylene glycol, triethylene glycol, dipropylene glycol, 1,3-butylene glycol and hexylene glycol (2-methyl-2,4-pentandiol) as examples of higher glycols may be found.

The used technical fluids mentioned normally include 10% by weight or more of water, especially 50% by weight or more of water with antifreeze, the bulk of which should preferably be removed by distillation prior to glycol recovery. The distillative removal of water is carried out either by concentrating under reduced pressure and hence at temperatures where the thermal stress is only small; or else by likewise separating off the water by azeotropic entrainment, advantageously with the same solvent or the same solvent mixture as also used for entraining the glycol.

During the azeotropic entrainment of glycols, the additives and specific contaminants present in the used technical fluids gradually separate out, but do not clump or cake; stirring is possible, if necessary. In fact, these ingredients are obtained as a readily stirrable and pumpable but also filterable suspension in the particular entrainer. Nor is there any interference here from subsequently added components, for example alkali metal hydroxides added for avoiding nitrosamine formation in antifreeze or for hydrolyzing dialkyl terephthalates as an example.

The glycol phase isolated in this way does already largely consist of the product of value and additionally contains at most only traces of the entrainer, which can be removed by simple means (stripping or distillation). The entrainer can be freed of the precipitated additives by filtration or, by addition of water to dissolve the additives and removal of the aqueous phase, recovered and re-used.

The process of the present invention yields pure, colorless and in particular odorless recovered glycols which are suitable for renewed use in the corresponding technical process, especially in antifreeze. The present invention therefore also provides for the use of the glycols recovered according to the invention in the corresponding technical process, especially in antifreeze.

The present invention also relates to a process for recovering glycols from used glycol-containing technical fluids obtained in the manufacture of polyester fibers.

EXAMPLE 8000 g of a used automotive antifreeze having an ethylene glycol content of about 40% by weight were admixed with from 15 to 20 g of NaOH and substantially freed of the water content at from 200 to 300 mbar and a maximum temperature of 150° C. to give about 3600 g of a concentrated mixture.

1000 g of this mixture were introduced together with 500 g of technical grade xylene into a suitable continuous azeotropic distillation apparatus fitted with a separator head (condenser, phase separator, return to distillation flask). The remainder of the concentrate was gradually added in the course of the distillation.

On completion of the distillation about 3200 g had been obtained of the separated-of f glycol phase with an ethylene glycol content of 95% by weight. The rest was made up of propylene glycol and diethylene glycol.

To obtain ethylene glycol of higher purity, a fractional distillation can be added.

We claim:

1. A process for recovering a glycol from a used glycol-containing technical fluid, which comprises adding to the used glycol-containing technical fluid an alkali metal hydroxide and an organic solvent which forms, with the glycol, an azeotropic mixture which has a lower boiling point than the glycol itself and distilling off this azeotropic mixture, wherein the used glycol-containing technical fluid is used antifreeze.

2. A process as claimed in claim 1 wherein the organic solvent is a xylene or a pseudocumene.

3. A process as claimed in claim 1 wherein said glycol is ethylene glycol.

4. A process as claimed in claim 1 wherein said glycol is a higher glycol.

5. A process as claimed in claim 1 wherein before the addition of the organic solvent which forms an azeotropic mixture with the glycol, the main portion of any water in the used glycol-containing technical fluid is removed by distillation.

* * * * *